United States Patent [19]

Kyle et al.

[11] 4,220,814
[45] Sep. 2, 1980

[54] TERMINAL FOR MEDICAL INSTRUMENT AND METHOD OF ASSEMBLING THE TERMINAL

[75] Inventors: James C. Kyle, Mission Viejo; Donald F. Cook, San Juan Capastrano, both of Calif.

[73] Assignee: Medical Components Corp., Mission Viejo, Calif.

[21] Appl. No.: 870,192

[22] Filed: Jan. 17, 1978

[51] Int. Cl.$^2$ .................... H01B 17/26; A61N 1/36
[52] U.S. Cl. ..................... 174/152 GM; 65/59 R; 128/419 P; 174/50.61; 428/432
[58] Field of Search ......... 174/152 GM, 50.61, 50.58, 174/50.63; 228/122, 903; 428/432, 433, 434; 403/179, 29, 30, 28; 65/59 R, 59 B; 128/419 P

[56] References Cited

U.S. PATENT DOCUMENTS

| | | | |
|---|---|---|---|
| 1,906,816 | 5/1933 | Schmidt, Jr. | 174/152 GM |
| 3,320,557 | 5/1967 | Garstang | 361/302 X |
| 3,920,888 | 11/1975 | Barr | 174/152 GM |
| 4,072,154 | 2/1978 | Anderson et al. | 128/419 P |
| 4,152,540 | 5/1979 | Duncan et al. | 174/152 GM |

Primary Examiner—Roy N. Envall, Jr.
Assistant Examiner—E. F. Borchelt
Attorney, Agent, or Firm—Ellsworth R. Roston

[57] ABSTRACT

A terminal is provided for introducing signals from an electrical terminal pin in a heart pacemaker to a terminal lead introduced into a patient's body. The terminal pin is disposed in a lid of the heart pacemaker so that the terminal pin is insulated from the lid. Means are also provided for introducing the signals on the terminal pin to the terminal lead without subjecting the pin to undue stresses.

The terminal includes a hollow, electrically conductive ferrule disposed in concentric relationship with the terminal pin and attached to the lid. An electrical filter is disposed in the ferrule and is maintained in fixed relationship to the ferrule and the terminal. Insulating means are provided for bonding the ferrule and the terminal.

An elongated sleeve is disposed on the ferrule and an insulating material is disposed between the terminal pin and the sleeve and is hermetically sealed to the terminal pin and the sleeve. The sleeve supports an electrically conductive catheter block which fits over the electrical terminal pin and communicates electrically with the terminal pin. The catheter block also holds the terminal lead in fixed position and communicates electrically with the lead and directs the lead into the body of the patient.

A method is also provided for assembling the terminal. The method provides for the assembly of the terminal in a minimum number of steps and in a manner to insure the proper assembly of the terminal without breaking any components in the terminal.

40 Claims, 5 Drawing Figures

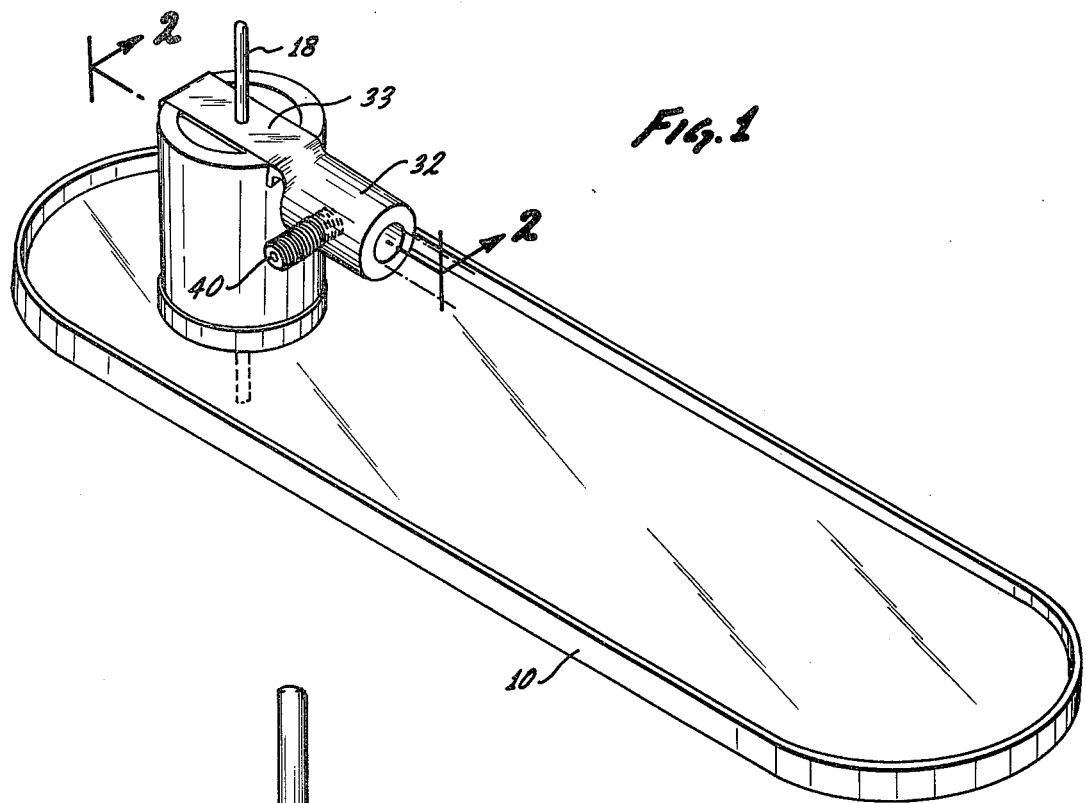
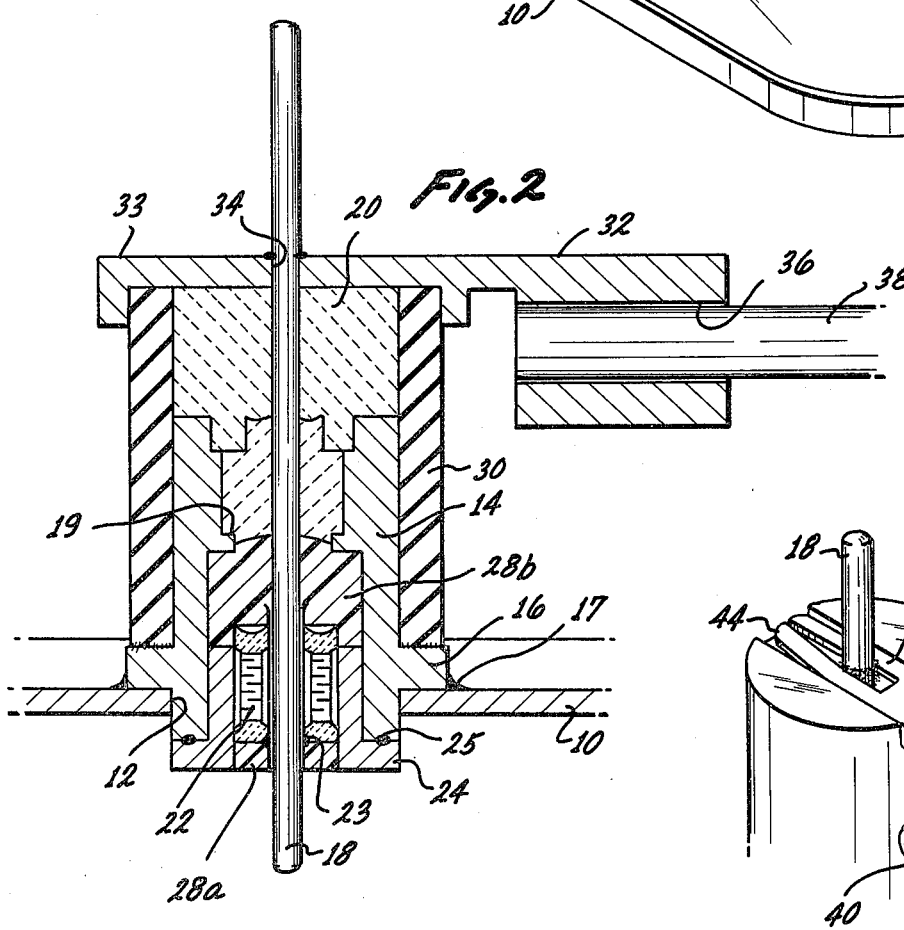
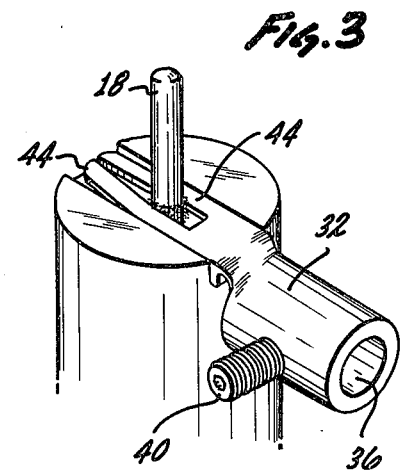

TERMINAL FOR MEDICAL INSTRUMENT AND METHOD OF ASSEMBLING THE TERMINAL

This invention relates to a terminal for maintaining an electrical terminal pin in insulated relationship to a lid on a housing for a heart pacemaker and for introducing signals from the electrical terminal pin to a terminal lead passing into the patient's body. More particularly, the invention relates to a terminal for maintaining the electrical terminal pin in insulated relationship to the lid and for providing for the introduction of signals from the terminal pin to the terminal lead without any bending or breaking of the terminal pin and without destroying the hermetic relationship produced in the terminal. The invention further relates to a method of assembling the terminal in a mininum number of steps and in an efficient manner.

In recent years, considerable advances have been made in medical technology involving the treatments of patients with heart problems. For example, patients having defective hearts have received heart pacemakers which produce signals at a particular frequency and stimulate the heart so that the heart pumps blood through the patient at that frequency. Initially, the heart pacemakers were disposed externally. However, with recent advances in the construction of the heart pacemakers and in medical technology, the heart pacemakers are now often disposed within the body of the patient.

In spite of the considerable advances which have been made, some problems still exist in heart pacemakers. For example, the electrical terminal pin providing signals to the heart is still not disposed relative to the lid and housing of the heart pacemaker so that a hermetic seal is maintained between the terminal pin and the lid. As will be appreciated, if a hermetic seal is not maintained between the terminal pin and the lid, the terminal pin will not be maintained in electrically insulated relationship to the lid so that the introduction of signals from the terminal pin to the heart of the patient deteriorates.

Another problem in heart pacemakers has been that the electrical terminal pins tend to become bent or broken when a catheter block has been inserted into the body of the patient to provide for the introduction of signals from the terminal through an electrical lead to the patient's heart. This has resulted in part because the electrical terminal pin has not been properly supported relative to the lid. When the terminal pins become bent, the insulating relationship between the terminal pin and the lid and the hermetic seal in the terminal tend to become destroyed. As a result, malfunctions of the pacemaker have occurred.

Considerable effort has been made to solve the problems discussed in the previous paragraphs. For example, a considerable effort has been made to insure that a hermetic seal is maintained between the electrical terminal and the lid when the heart pacemaker is inserted into a patient's body. A considerable effort has also been made to prevent the electrical terminal pin from becoming bent or broken and the hermetic seal in the terminal from becoming destroyed when a catheter block is inserted into the body of a patient and is coupled to the terminal pin. In spite of these considerable efforts, the problems discussed above still exist to a pronounced effect in heart pacemakers.

In copending application Ser. No. 836,657 filed by James C. Kyle in the United States Patent Office on Sept. 26, 1977, for a "Terminal for Medical Instrument" and assigned of record to the assignee of record of this application, a terminal is disclosed which overcomes the above difficulties. The terminal disclosed and claimed in application Ser. No. 836,657 provides a hermetic seal and is effective in preventing the terminal pin from being broken.

This invention provides a terminal which also overcomes the problems discussed above and which may be even more effective than the terminal disclosed and claimed in application Ser. No. 836,657 in preventing the terminal pin from being broken. For example, the terminal of this invention provides and maintains a hermetic seal between the terminal pin and the lid to insure that the terminal pin is in electrically isolated relationship to the lid and that no leakage of fluid can occur into or out of the heart pacemaker. Furthermore, the apparatus provides for the insertion of a catheter block (or electrical body) into the body of a patient and for the coupling of the catheter block to the electrical terminal pin without bending or breaking the electrical terminal pin and without destroying the hermetic seal. In this way, the terminal of the invention insures that electrical signals are introduced, without any deterioration in quality, from the pacemaker into the patient's heart.

The apparatus includes a hollow, electrically conductive ferrule disposed in concentric relationship with the electrical terminal pin. The ferrule is provided with a flange which is disposed against the lid to maintain the ferrule in a particular relationship to the lid. An electrical filter may be disposed in the ferrule to pass signals having only a particular frequency to the electrical terminal for introduction to the patient's heart. Means are provided for maintaining the filter in fixed and insulated relationship to the ferrule and the terminal pin. Insulating means are provided for bonding to the ferrule and the terminal pin.

An elongated sleeve is disposed on the ferrule and insulating material is disposed between the terminal pin and the sleeve and between the terminal pin and the ferrule and is hermetically sealed to the terminal pin, the ferrule and the sleeve. The sleeve supports a catheter block (or electrical body) at the end of the sleeve opposite to the lid. The catheter block fits over the electrical terminal pin and communicates electrically with the terminal pin. The catheter block also holds the terminal lead in fixed position and communicates electrically with the terminal lead and directs the terminal lead into the body of the patient.

In one embodiment, a compressible seal is disposed in the terminal and is compressed upon the assembly of the parts comprising the terminal. The compression of the seal facilitates the production of a hermetic relationship in the terminal. An induction coil is disposed in the seal and is connected to the filter and the terminal pin to facilitate the filtering of signals introduced into the patient's body.

The invention also relates to methods of easily and efficiently assembling the terminal assembly so that a hermetic seal is produced. By the methods constituting this invention, the steps of assembling and hermetically sealing the parts insure that the parts will be properly assembled and the hermetic seal will not be broken.

In the drawings:

FIG. 1 is a perspective view of a lid for the housing of a heart pacemaker and an electrical terminal for maintaining a terminal pin in the terminal in insulated relationship to the lid and for introducing signals from the pacemaker through the terminal pin and into the body of a patient;

FIG. 2 is a sectional view substantially on the line 2—2 of FIG. 1 and shows the terminal of FIG. 1 in further detail;

FIG. 3 is a perspective view of a modification of one of the features shown in the previous Figures;

Figure 4:
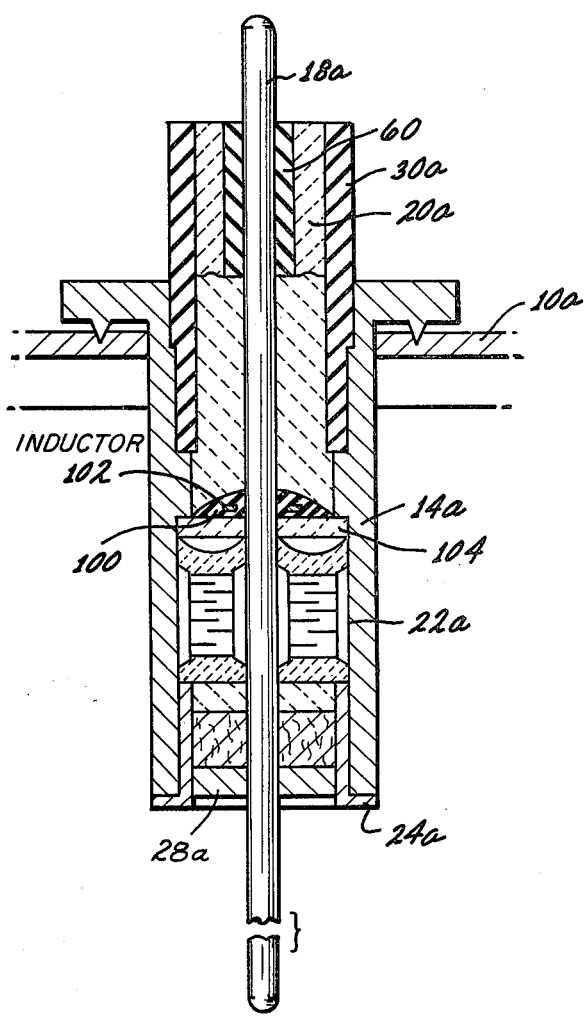
FIG. 4 is a sectional view similar to that of FIG. 2 but showing another embodiment of the invention.

In one embodiment of the invention, a lid 10 is provided with an aperture 12. A ferrule 14 having a hollow cylindrical configuration is disposed within the aperture 12 and is provided with a flange 16 which rests on the lid 10. The flange 16 of the ferrule 14 is welded as at 17 to the lid 10 around the periphery of the flange. The ferrule 14 may be made from a suitable material such as titanium or stainless steel. The ferrule 14 may also be made from a material designated as a "multi-phase alloy" by Latrobe Steel of Pittsburgh, Pa.

An electrical terminal pin 18 made from a suitable material such as platinum is disposed within the ferrule 14 in concentric relationship to the ferrule. The terminal pin 18 may also be made from the material designated as "a multi-phase alloy" by Latrobe Steel. The terminal pin 18 is hermetically sealed to the ferrule 14 by a suitable material 20 which is seated on an internal flange 19 in the ferrule 14. The material 20 may constitute a standard glass-to-metal seal. Preferably, however, the material 20 may constitute a seal such as disclosed and claimed in application Ser. No. 836,659 filed by James C. Kyle on Sept. 26, 1977, for a "Ceramic Seal and Method of Making Such Seal" and assigned of record to the assignee of record of this application. Glass, and particularly the material disclosed in copending application Ser. No. 836,659, are advantageous because they provide a high electrical impedance, produce a long path for the flow of electrical leakage current between the ferrule 14 and the terminal pin 18 and maintain a hermetic seal between the pin and the ferrule even when the pin is subjected to considerable bending and twisting forces. The insulating material disclosed and claimed in application Ser. No. 836,659 is also advantageous because it has a thermal coefficient of expansion relative to those of the terminal pin 18 and the ferrule 14 for maintaining the hermetically sealed relationship with changes in temperature. The seal 20 is disposed in contiguous relationship to an internal flange on the ferrule 14.

An electrical filter 22 is also disposed on the terminal 18 within the hollow configuration of the ferrule 14. The filter 22 has characteristics for passing signals only in a range of approximately 10 megahertz. For example, the filter 22 may have 6 db characteristics at approximately 10 megahertz, 40 db characteristics at approximately 100 megahertz and 60 db characteristics at approximately 1 gigahertz. As shown in FIG. 2, the filter 22 may be disposed at least partially within the heart pacemaker. The filter 22 may be constructed in a conventional manner from a plurality of spaced plates or discs to define a capacitive filter. The filter 22 may be attached to the terminal pin 18 as a solder at 23.

The filter 22 is maintained in fixed relationship within the ferrule 14 by a spacer 24 made from a suitable material such as a stainless steel (if the ferrule is made of stainless steel) or made of nickel or a nickel-iron-cobalt alloy designated by the trademark "Kovar" (if the ferrule is made of titanium). The spacer 24 is provided with a hollow cylindrical body and with a flange which is disposed against the bottom of the ferrule 14. The spacer 24 is attached to the ferrule 14 at 25 as by projection welding. Projection welding is desirable since it provides localized heating without affecting the solder attachment 23.

A suitable adhesive such as a thermal-setting epoxy is disposed as fillers 28a and 28b on opposite sides of the filter 22 to maintain the filter in fixed position relative to the ferrule. The epoxy may be purchased commercially. For example, a commercially granulated epoxy may be purchased from Hysol in Pasadena, California, for use as the epoxy materials 28a and 28b. The filler 28b is disposed at one end against the internal flange 19 on the ferrule 14.

An elongated sleeve 30 made from a suitable insulating material such as alumina or a polysulfide is disposed on the flange 16 of the ferrule 14 and is bonded to the ferrule by the application of heat at a particular temperature of approximately 600° F. The sleeve 30 has properties of being relatively inert from a chemical standpoint and being relatively strong from a mechanical standpoint. When the sleeve 30 is made from a polysulfide, a polysulfide designated as "Ryton R4" by Phillips Petroleum may be used. Such a polysulfide has the advantage of being chemically inert in the patient's body.

A catheter block (or electrical body) 32 made from a suitable material such as stainless steel or titanium or a suitable alloy such as that designated as "Elgiloy" alloy made by Elgin Watch Company or such as that designated as "Haynes 25" by the Haynes Stellite Company is disposed on the sleeve 30 at the end of the sleeve opposite from the lid 10. The body 32 is suitably attached as by welding or fusing to the sleeve 30. The electrical body 32 is provided with an extension 33 and an aperture 34 is provided in the extension so that the terminal pin 18 can extend through the electrical body. The terminal pin 18 is connected electrically to the electrical body as by welding.

The catheter block 32 is provided at one end with a cylindrical body 36. A terminal lead 38 is disposed in the bore 36 and is clamped against the wall of the electrical body 32 by an adjustable screw 40 which extends through the wall of the electrical body. The terminal lead 38 receives from the terminal pin 18 the signals which are introduced to the heart of the patient to maintain the heart beat at a particular frequency.

The components described above may be assembled in a number of different ways, all of which are within the scope of the invention. In all of the different methods described below, the sleeve 30 is suitably attached to the catheter block 32 and the combination is inverted so that the inverted sleeve 30 can serve as a well for receiving all of the different components forming the terminal.

One way of assembling the terminal is initially to fuse the insulating material 20 to the terminal pin 18 and the ferrule 14. The sleeve 30 may then be brazed or bonded to the catheter block 32. When the sleeve 30 is made from a material such as alumina, it is brazed to the catheter block 32. However, when the sleeve 30 is made from a suitable material such as a polysulfide, it may be bonded to the catheter block 32 as by a high temperature epoxy. The combination of the catheter block 32 and the sleeve 30 may then be inverted from the position shown in FIG. 1 and the components may be assembled properly within the well defined by the inverted sleeve 30. The lid 10 may be attached to the flange 16 on the ferrule 14 as by welding by an electron beam and the insulating material may then be fused to the sleeve 30 and the catheter block 32. The terminal pin 18 may then be attached to the catheter block 32 as by electron welding as shown in FIG. 2.

Another way of assembling the terminal also includes the step of initially fusing the insulating material 20 to the terminal pin 18 and the ferrule 14. The lid 10 is then attached to the ferrule 14 as described above. The sleeve 30 is attached to the catheter block 32 in the manner described above and this combination is inverted as described above. All of the parts are then assembled in the well defined by the inverted sleeve 30. The assembly is then fired in a furnace to seal hermetically the combination of the sleeve 30 and the catheter block 32 to the sub-assembly of the terminal pin 18, the ferrule 14 and the insulating material 20. The terminal pin 18 may then be attached to the catheter block 32 as by electron welding.

A third way also includes the step of suitably attaching the sleeve 30 to the catheter block 32. The combination of the sleeve 30 and the catheter block 32 is then inverted as described above so that the sleeve serves as a well. The various components including the terminal pin 10, the ferrule 14 and the insulating material 20 are then positioned properly in the well. The assembly is then fired so that the insulating material 30 becomes fused to the terminal pin 18, the ferrule 14 and the catheter block 32 to define a unitary structure.

The lid 10 may then be attached to the ferrule 14 as by electron welding and the terminal pin is attached to the catheter block 32 as by electron welding.

The methods described above offer certain important advantages. By attaching the sleeve 30 and the catheter block 32 and then inverting the combination, the sleeve 30 is able to serve as a well for receiving all of the components in the assembly. This provides for a convenient insertion of the components into the sleeve and facilitates proper positioning of the components relative to one another. Furthermore, all of the components can be easily retained in position during the time that they are fused to produce the hermetic seal. In this way, the assembly and sealing of the terminal are facilitated by the methods constituting this invention.

Instead of extending the terminal pin 18 through the aperture 34 in the extension 33 of the catheter block 32 as shown in FIG. 2, the terminal pin 18 can be attached to the catheter block 32 as shown in FIG. 3. In the modification shown in FIG. 3, a pair of resilient prongs 44 are provided at the end of the catheter block. The terminal pin 18 is inserted between the prongs 44 and the terminal pin is then attached to the prongs as by welding by an electron beam.

The invention described above has certain important advantages. It provides a hermetic seal between the terminal pin 18 and the ferrule 14 and between the terminal pin 18 and the sleeve 30 and between the terminal pin 18 and the lid 10. It also provides a high electrical impedance between the terminal pin 18 and the lid 10 and maintains this impedance because of the hermetic seal produced between the terminal pin 18 and the lid 10 by the bonding of the insulating material 20 to these members. It provides within the ferrule a filter which regulates the frequency of the signals introduced from the heart pacemaker to the electrical terminal pin 18 and then into the body of the patient through the lead 38.

The invention described above also has other important advantages. For example, the electrical body 32 can be attached to the terminal pin 18 without bending or breaking the terminal pin or without stressing the hermetic seal provided between the terminal pin and the ferrule 14 by the fusing of the insulation 20 to these members. The formation of this hermetic seal is facilitated by the use of the methods described above for assembling the terminal. This hermetic seal is maintained even when the terminal pin 18 is subjected to considerable bending and twisting forces. Furthermore, even if the terminal should be fractured or broken at a position above the internal flange 19 in the ferrule 14, the hermetic seal would still be maintained for the critical parts because the terminal pin 18, the ferrule 14 and the filter 22 would still be hermetically sealed.

By providing the arrangement described above and shown in the drawings, mechanical forces imposed upon the catheter block 32 are transferred from the catheter block to the sleeve 30 and then by the sleeve to other members including the ferrule 14. In this way, the lid assembly constituting this invention is capable of withstanding any bending forces and shields the terminal pin 18 from any such bending forces. This causes the hermetic seal in the terminal to be maintained and the high electrical insulation between the terminal pin 18 and the ferrule 14 and between the terminal pin 18 and the lid 10 to be preserved.

The method described above can be modified as shown in FIG. 4 without departing from the scope of the invention. This modification involves the inclusion of a collar 60 (FIG. 4) which is made from a suitable insulating material such as alumina and which is disposed on the terminal pin 18 at the end opposite the lid 10. The use of such a collar 50 is advantageous because it facilitates the creation of a hermetic seal between the terminal pin 18, the ferrule 14 and the catheter block 32 when the insulating material 20 is fused.

When the collar 60 is included, the insulating material 20 may be first inserted in the space below the collar to fill the space between the terminal pin 18 and the ferrule 14 and this insulating material may be fired to fuse the collar, the terminal pin and the ferrule. After the sub-assembly of the insulating material 20, the collar 60, the terminal pin 18 and the ferrule 14 has been inserted into the well defined by the inverted sleeve 30, additional insulating material may be inserted into the space between the collar 60 and the sleeve 30 and the assembly may be fired to fuse the insulating material to the sleeve 30, the collar 60 and the catheter block 32.

The embodiment shown in FIG. 4 is similar to the embodiment shown in FIGS. 1, 2 and 3 and accordingly includes numerical designations similar to those for the previous embodiment except that the letter "a" follows these numerical designations. Furthermore, in the embodiment shown in FIG. 4, the sleeve 30a is disposed within the ferrules 14a. The embodiment shown in FIG. 4 also includes a seal 100 made from a suitable compressible material having insulating properties. Silicone rubber has been found to be entirely adequate for the seal 100. The seal 100 may be disposed above the filter 22a and may be compressed when the spacer 24a is disposed in position against the flange on the ferrule. By compressing the seal 100, the sleeve presses against the terminal pin 18a and the ferrule 14a and facilitates the production of hermetic seals with these members.

An inductance 102 may be disposed within the seal 100. The inductance may be made from a suitable material such as ferrite having a high mu or a powdered nickel and may be in the shape of a disc or a doughnut. The inductance 102 cooperates with the capacitive filter 22a to prevent the introduction of extraneous signals to the heart pacemaker. For example, the inductance 102 may be in series with the terminal pin 18a and the filter 22 may be disposed electrically between the terminal and ground.

Instead of providing the seal 100 and the inductance 102 as separate elements, particles of material with magnetic properties may be dispersed throughout the compressible material defining the seal. This tends to simplify the manufacture of the seal 100 and the inductance 102.

A suitable hermetic seal 104 may be provided directly above the filter 22a. The hermetic seal 104 may be made from a suitable glass or from a material disclosed and claimed in copending application Ser. No. 836,657 and assigned of record to the assignee of record in this application. The inclusion of the seal 104 facilitates the retention of a high insulating relationship between the terminal pin 18a and the ferrule 14a and the electrical isolation of the filter 22a from the terminal and the ferrule. It also prevents chemicals from the patient's body from affecting the operating characteristics of the terminal.

As will be seen from one embodiment shown in FIG. 4, substantially all of the elements within the lid assembly are disposed below the lid 10a. This is advantageous because the elements below the lid 10a are effectively sealed and accordingly are not affected by such atmospheric elements as moisture.

Figure 5:
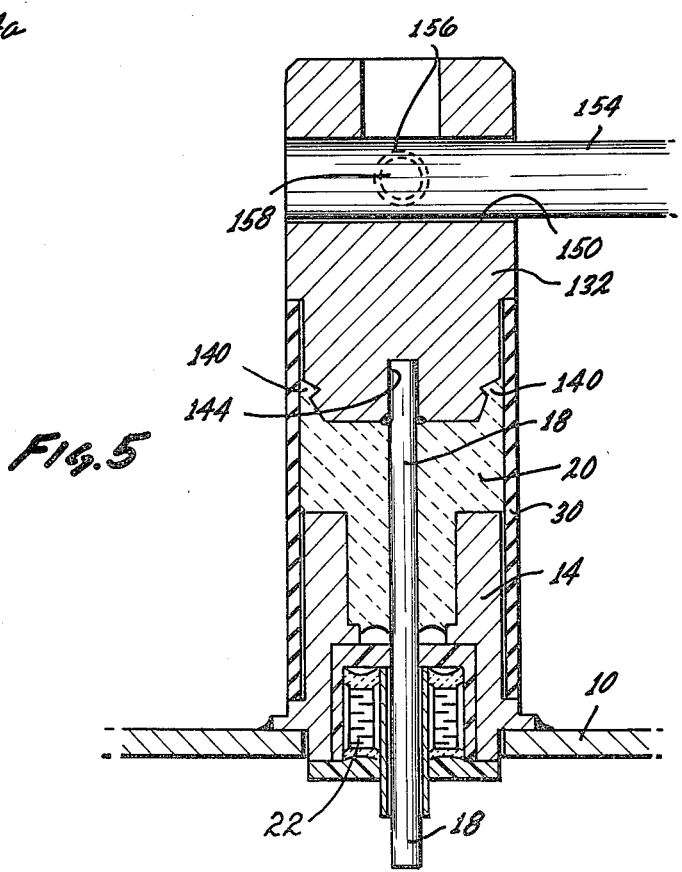
FIG. 5 is a sectional view of another embodiment of the invention.

The embodiment shown in FIG. 5 is similar in many respects to the embodiment shown in FIGS. 1 and 2 in that it includes the ferrule 14, the terminal pin 18, insulating material 20 and the sleeve 30. The sleeve 30 in FIG. 5 is also elongated in a manner similar to the sleeve 30 in FIGS. 1 and 2. The sleeve 30 extends into a catheter block 132 disposed above the sleeve in coaxial stud-mounted feed-through relationship with the sleeve. The catheter block 132 is retained in position by the sleeve and by detents 140 in the insulating material 20.

The catheter block 132 is suitably connected to the terminal pin 18. For example, this connection may be made by disposing the terminal pin 18 in a socket 144 in the catheter block 132. The terminal pin and the socket 144 may be threaded to provide a mating relationship. Alternatively, the terminal pin may be welded as by an electron beam to the catheter block 132 at the base of the socket 144.

The catheter block 132 may be provided with an aperture as at 150 to receive a lead 154 which introduces signals to a patient's heart to maintain the heart beat of the patient at a particular rate. A tapped bore 156 extends through the catheter block 132 in a direction transverse to the aperture 154 and communicates with the aperture. A holding screw 158 is threaded into the bore 156 and is tightened against the lead 154 to hold the lead in fixed position.

As will be seen, the catheter block 132 in FIG. 5 is not disposed as close to the lid 10 as is the catheter block in FIGS. 1 and 2. However, the disposition of the catheter block 132 in coaxial relationship with the sleeve 30 does offer certain advantages. For example, the forces imposed upon the terminal of FIG. 5, and particularly on the catheter block of FIG. 5, are more balanced than those imposed on the catheter block of FIGS. 1 and 2.

The disposition of the catheter block coaxially on the sleeve as in FIG. 5 also tends to offer some mechanical protection to the sleeve and to the components within the sleeve.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In combination for providing for the introduction of a terminal lead from a heart pacemaker into the body of a patient,
   a lid for the heart pacemaker,
   an electrical terminal pin,
   means for supporting the terminal pin in electrically insulated relationship to the lid including
   first support means enveloping the electrical terminal pin and disposed in spaced relationship to the terminal pin and engaging the lid,
   second support means supported by the first support means in insulated relationship to the lid and extending above the first support means,
   insulating means disposed between the terminal pin and the first support means and between the terminal pin and the second support means and hermetically sealed to the first support means, the second support means and the terminal pin for maintaining the terminal pin in fixed and spaced relationship to the first and second support means, the insulating means being disposed relative to the terminal pin and the lid for providing a long path for the leakage of electrical current between the terminal pin and the lid to maintain the terminal pin in electrically insulated relationship to the lid, and
   electrical body means disposed on the second support means and hermetically sealed to the insulating means and electrically connected to the terminal pin and retaining the terminal pin in electrically conductive relationship with the terminal lead for introducing signals from the terminal pin through the terminal lead into the body of the patient.

2. The combination set forth in claim 1 wherein
   the terminal pin extends through the electrical body means and the electrical body means rests on the second support means and wherein the second support means rests on the first support means.

3. The combination set forth in claim 1 wherein
   an electrical filter is disposed within the first support means in a fixed relationship to the first support means and is provided with characteristics to pass to the patient from the heart pacemaker electrical signals having only particular frequencies.

4. The combination set forth in claim 3 wherein
   the first support means is provided with a flange having first and second opposite surfaces and the lid is disposed against the first surface of the flange and is attached to the flange and the second support means is disposed against the second surface of the flange and wherein the electrical filter is positioned for disposition at least partially within the heart pacemaker.

5. The combination set forth in claim 3 wherein
   the first support means is provided with an internal shoulder and the insulating means is seated on the shoulder and the insulating means is also fused to the terminal pin and is provided with a coefficient of thermal expansion relative to those of the first support means, the terminal pin and the second support means to maintain the first support means, the terminal pin and the second support means in fused relationship with changes in temperature.

6. The combination set forth in claim 3 wherein the electrical filter is capacitive and an inductance is disposed within the first support means and is connected electrically to the electrical filter to facilitate the passage to the patient from the heart pacemaker only of electrical signals having the particular frequencies.

7. The combination set forth in claim 6 wherein the inductance is disposed in a compressible seal and the seal is compressed when the first support means is disposed in electrically insulated relationship to the lid.

8. The combination set forth in claim 1 wherein
the second support means has an extended length for serving as a well to retain the first support means and the insulating means.

9. In combination for providing for introduction of a terminal lead from a heart pacemaker into the body of a patient,
a lid,
an electrical terminal pin,
a ferrule made from an electrically conductive material and having a hollow configuration and disposed in spaced relationship to the terminal pin and supported by the lid,
an electrical filter disposed in concentric relationship to the terminal pin and within the ferrule and having properties of passing signals only within a particular range of frequencies,
first means disposed within the ferrule for maintaining the electrical filter in fixed relationship to the terminal pin and the ferrule,
second means having insulating properties and disposed on the ferrule and extending above the ferrule,
insulating means disposed between the ferrule and the terminal pin and hermetically sealing the terminal pin, the ferrule and the second means, and
electrical body means disposed on the second means for supporting the terminal lead and hermetically sealed to the insulating means and connected electrically to the terminal pin for introducing the electrical signals on the terminal pin through the terminal lead into the body of the patient.

10. The combination set forth in claim 9 wherein
the insulating means is fused to the ferrule and the terminal pin and the second means and the electrical body means and is provided with a thermal coefficient of expansion relative to those of the terminal pin and the ferrule and the second means and the electrical body means for maintaining this fused relationship with changes in temperature.

11. The combination set forth in claim 9 wherein a compressible seal is disposed within the ferrule and is compressed by the first means to facilitate the production of a hermetic seal between the terminal pin and the ferrule and the disposition of the filter in the ferrule in a hermetically sealed relationship to the terminal pin and the ferrule.

12. The combination set forth in claim 11 wherein an inductance is disposed in the compressible seal and the filter is capacitive and the inductance is connected to the filter and is provided with characteristics relative to those of the filter to facilitate the passage of signals only within the particular range of frequencies.

13. The combination set forth in claim 9 wherein
the filter is positioned for disposition at least partially within the heart pacemaker and the ferrule is provided with a flange having first and second opposite surfaces and the lid is disposed against the first surface of the flange on the ferrule and is attached to the flange and the second means is disposed at one end against the second surface of the flange on the ferrule and the electrical body means is disposed against the other end of the second means and the ferrule is provided with an internal shoulder and the insulating means is seated on the shoulder.

14. In combination for providing for the introduction of a terminal load from a heart pacemaker into the body of a patient,
a lid,
an electrical terminal pin,
a ferrule made from an electrically conductive material and having a hollow configuration and disposed in spaced relationship to the terminal pin and supported by the lid,
a filter disposed on the terminal pin and within the ferrule,
a sleeve made from an electrically insulating material and disposed on the ferrule,
insulating means maintaining the electrical terminal pin, the filter, the sleeve and the ferrule in spaced and hermetically sealed and electrically insulating relationship and providing a long path for the flow of leakage current between the terminal pin and the ferrule, and
an electrically conductive catheter block disposed on the sleeve in electrically communicating relationship with the terminal pin and hermetically sealed by the insulating means and supported by the sleeve and engaging the terminal lead in a fixed relationship to provide for the introduction of electrical signals from the terminal pin to the terminal lead.

15. The combination set forth in claim 14 wherein
the electrically conductive catheter block rests on the sleeve at a position displaced from the lid and from the ferrule and wherein means are provided in the catheter block for maintaining the terminal lead in fixed relationship to the block and in electrically communicating relationship with the block.

16. The combination set forth in claim 15 wherein a compressible seal is disposed within the ferrule between the filter and the insulating means and means are attached to the ferrule to compress the seal for facilitating the production of a hermetic seal between the terminal pin and the ferrule.

17. The combination set forth in claim 14 wherein
the insulating means is fused to the ferrule and the terminal pin and the catheter block and is provided with a thermal coefficient of expansion relative to those of the terminal pin and the ferrule and the catheter block for maintaining this fused relationship with changes in temperature.

18. The combination set forth in claim 14 wherein an inductance is disposed within the ferrule, and is connected electrically to the filter and the filter is provided with capacitive properties and the inductance and the filter are provided with properties to pass only signals within a particular range of frequencies to the terminal lead.

19. The combination set forth in claim 14 wherein the filter is positioned for disposition at least partially within the heart pacemaker and the ferrule is provided with a flange having first and second opposite surfaces and the lid is disposed against the first surface of the flange and is attached to the flange and the sleeve is disposed at one end against the second surface of the flange and the catheter block is disposed against the other end of the sleeve.

20. The combination set forth in claim 19 wherein the ferrule is provided with an internal shoulder and the insulating means is hermetically sealed to the internal shoulder.

21. In combination for providing for the introduction of a terminal lead from a heart pacemaker into the body of a patient,
   a terminal pin,
   first support means having electrically conductive properties and spaced from the terminal pin,
   a lid disposed in abutting relationship to the first support means,
   an electrical body for supporting the terminal lead and coupled electrically to the terminal pin, and
   insulating means disposed between the terminal pin and the first support means and hermetically sealing the terminal pin, the first support means and the electrical body.

22. The combination set forth in claim 24, including,
   second support means engaging the first support means and the electrical body and hermetically sealed to the insulating means.

23. The combination set forth in claim 22 wherein the first support means is provided with an internal shoulder and the insulating means is disposed against the internal shoulder and the second support means is seated on the internal shoulder.

24. The combination set forth in claim 21, including,
   a filter disposed within the first support means at a position for disposition within the heart pacemaker.

25. The combination set forth in claim 24 wherein second support means are provided and wherein the second support means engage the first support means and the electrical body and the insulating means hermetically seals the second support means and an inductance is disposed within the first support means and the filter is capacitive and the inductance is connected electrially to the filter.

26. The combination set forth in claim 25 wherein the first support means has a flange defined by first and second opposite surfaces and the lid is disposed against the first surface of the flange and the second support means is disposed at one end against the second surface of the flange and the second support means is provided with electrically insulating properties.

27. The combination set forth in claim 21 wherein the first support means is provided with an internal shoulder and an insulating sleeve is seated on the internal shoulder of the first support means and is provided with an extended length to define a well and the electrical body is disposed against the insulating sleeve and the insulating means is disposed in the well defined by the insulating sleeve and the insulating means hermetically seals the insulating sleeve.

28. In combination for providing for the introduction of a terminal lead from a heart pacemaker into the body of a patient,
   a terminal pin,
   an electrically conductive ferrule disposed in spaced relationship to the terminal pin,
   an electrical body constructed to support the terminal lead, the electrical body being coupled electrically to the terminal pin,
   a lid disposed against the ferrule and coupled electrically to the ferrule, and
   insulating means hermetically sealing the terminal pin, the ferrule and the electrical body and having a high dielectric constant of electrical impedance to insulate electrically the terminal pin and the electrical body relative to the ferrule and the lid.

29. The combination set forth in claim 28, including,
   a sleeve made from insulating material and disposed on the ferrule and hermetically sealed by the insulating means.

30. The combination set forth in claim 29, including,
   the ferrule having a flange with first and second opposite surfaces and the lid being disposed against the first surface of the flange and the sleeve being disposed against the second surface of the flange.

31. The combination set forth in claim 29 wherein the electrically conductive body is disposed on the insulating sleeve and wherein the ferrule is provided with a flange and the lid is disposed against the flange on the ferrule.

32. The combination set forth in claim 31 wherein the insulating means hermetically seals the terminal pin, the ferrule, the electrically conductive body and the insulating sleeve.

33. The combination set forth in claim 31 wherein a filter is disposed on the terminal pin at a position within the ferrule and the insulating means seals the filter within the ferrule.

34. The combination set forth in claim 32 wherein a filter is disposed on the terminal pin at a position within the ferrule and is capacitive, and an inductance is also disposed within the ferrule and is electrically connected to the filter to define a tuned circuit and the insulating means hermetically seals the filter and the inductance within the ferrule.

35. The combination set forth in claim 28 wherein the ferrule is provided with an internal flange and the insulating means is seated against the internal flange and is hermetically sealed to the internal flange.

36. The combination set forth in claim 35 wherein a sleeve made from an insulating material is disposed on the ferrule and is hermetically sealed to the insulating means and a filter is disposed within the ferrule.

37. The combination set forth in claim 36 wherein the ferrule is provided with an external flange with first and second opposite surfaces and the lid is disposed against the first surface of the external flange and the sleeve is disposed against the second surface of the external flange and an inductance is disposed in the ferrule and is connected electrically to the filter and the filter is capacitive.

38. The combination set forth in claim 28 wherein an insulating sleeve is disposed on the ferrule and is provided with an extended length to define a well and the insulating means is disposed in the well and the lid is disposed against the insulating sleeve.

39. The combination set forth in claim 38 wherein the ferrule is provided with an internal flange and the insulating sleeve is disposed on the internal flange of the ferrule and is hermetically sealed by the insulating means.

40. In combination for providing for the introduction of a terminal lead from a heart pacemaker into the body of a patient,
- a terminal pin,
- an electrically conductive ferrule disposed in spaced relationship to the terminal pin,
- an insulating sleeve supported on the ferrule and extending above the ferrule to define a well,
- insulating means supported within the well defined by the insulating sleeve and insulating the terminal pin and the ferrule,
- a lid for the heart pacemaker, the lid being disposed against the ferrule, and
- an electrically conductive body disposed on the terminal pin in electrically conductive relationship with the terminal pin and insulated by the insulating means.

* * * * *